US00PP18338P2

(12) United States Plant Patent
Whetman

(10) Patent No.: US PP18,338 P2
(45) Date of Patent: Dec. 18, 2007

(54) ***DIANTHUS* PLANT NAMED 'STRAWBERRY SORBET'**

(50) Latin Name: *Dianthus*
Varietal Denomination: Strawberry Sorbet

(76) Inventor: John Whetman, Deer Park Farm, Chudleigh, Newton Abbot Devon TQ13 ONH (GB)

( * ) Notice: Subject to any disclaimer, the term of this patent is extended or adjusted under 35 U.S.C. 154(b) by 165 days.

(21) Appl. No.: 11/325,148

(22) Filed: Jan. 3, 2006

(51) Int. Cl.
*A01H 5/00* (2006.01)

(52) U.S. Cl. ..... Plt./281

(58) Field of Classification Search ..... Plt./276
See application file for complete search history.

*Primary Examiner*—Wendy C. Haas
*Assistant Examiner*—Georgia Helmer

(57) ABSTRACT

A new cultivar of *Dianthus* plant named 'STRAWBERRY SORBET' that is characterized by pronounced compact habit, grey-green foliage, and bright red flowers. In combination these traits set 'STRAWBERRY SORBET' apart from all other existing varieties of *Dianthus* known to the inventor.

2 Drawing Sheets

Genus: *Dianthus*. Species: ×*hybrida*.
Denomination: STRAWBERRY SORBET.

BACKGROUND OF THE INVENTION

The present invention relates to a new and distinct cultivar of carnation that is grown for use as a flowering plant for pots and containers. The new cultivar is known botanically as *Dianthus*×*hybrida* and will be referred to hereinafter by the cultivar name 'STRAWBERRY SORBET'.

'STRAWBERRY SORBET' is a complex hybrid plant that is the product of a breeding program started by the inventor in 1985. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'STRAWBERRY SORBET' in 2001 for its unique pronounced compact habit accompanied by abundant bright red flowers that bloom from May through October.

'STRAWBERRY SORBET' is a dwarf carnation exhibiting pronounced compact habit, grey-green foliage, and bright red flowers. The surfaces of stems, leaves, calyx, and epicalyx all exhibits the characteristic waxy bloom of *Dianthus*. 'STRAWBERRY SORBET' is a complex hybrid plant that resulted from the open pollination between large families of seedlings from *Dianthus* 'Queen of Henri' (unpatented) and *Dianthus* 'Waithman's Beauty' (unpatented). The variety of *Dianthus* which is considered by the inventor to most closely resemble 'STRAWBERRY SORBET' is the inventor's variety *Dianthus* 'Spangled Star' (U.S. Plant Pat. No. 13,029). When compared to 'Spangled Star', 'STRAWBERRY SORBET' is more vigorous with larger flowers. 'STRAWBERRY SORBET' has a longer flowering period than 'Spangled Star'. The flowers of 'STRAWBERRY SORBET' are more red and pink in color than 'Spangled Star'.

Asexual reproduction of the new cultivar was first accomplished by the inventor in 2001 in a cultivated area of Houndspool, United Kingdom. The method of asexual propagation used was vegetative cuttings. Since that time the characteristics of the new cultivar have been determined stable and are reproduced true to type in successive generations of asexual reproduction.

SUMMARY OF THE INVENTION

The following traits have been repeatedly observed and represent the characteristics of the new *Dianthus* cultivar 'STRAWBERRY SORBET'. These traits in combination distinguish this cultivar from all other commercial varieties known to the inventor. 'STRAWBERRY SORBET' has not been tested under all possible conditions and phenotypic differences may be observed with variations in environmental, climatic and cultural conditions, however, without any variance in genotype.

1. *Dianthus* 'STRAWBERRY SORBET' exhibits a pronounced compact habit.
2. *Dianthus* 'STRAWBERRY SORBET' blooms profusely.
3. *Dianthus* 'STRAWBERRY SORBET' exhibits bright red flowers from May through October.
4. *Dianthus* 'STRAWBERRY SORBET' exhibits grey-green foliage.
5. At maturity, the height of the foliage mound of *Dianthus* 'STRAWBERRY SORBET' is 15 cm to 20 cm. The mature width is 20 cm to 30 cm.
6. *Dianthus* 'STRAWBERRY SORBET' is a herbaceous perennial.
7. *Dianthus* 'STRAWBERRY SORBET' is suitable for use as a flowering plant in pots, containers, window boxes and the garden.
8. *Dianthus* 'STRAWBERRY SORBET' is hardy to minus 15° Centigrade.

BRIEF DESCRIPTION OF THE DRAWINGS

The accompanying color drawings illustrate the overall appearance of the new *Dianthus* variety 'STRAWBERRY SORBET' showing colors as true as it is reasonably possible to obtain in colored reproductions of this type. Colors in the drawings may differ from the color values cited in the detailed botanical description, which accurately describe the actual colors of the new variety 'STRAWBERRY SORBET'.

The drawing labeled as FIG. 1 depicts the pronounced compact habit of 'STRAWBERRY SORBET'.

Figure 2:
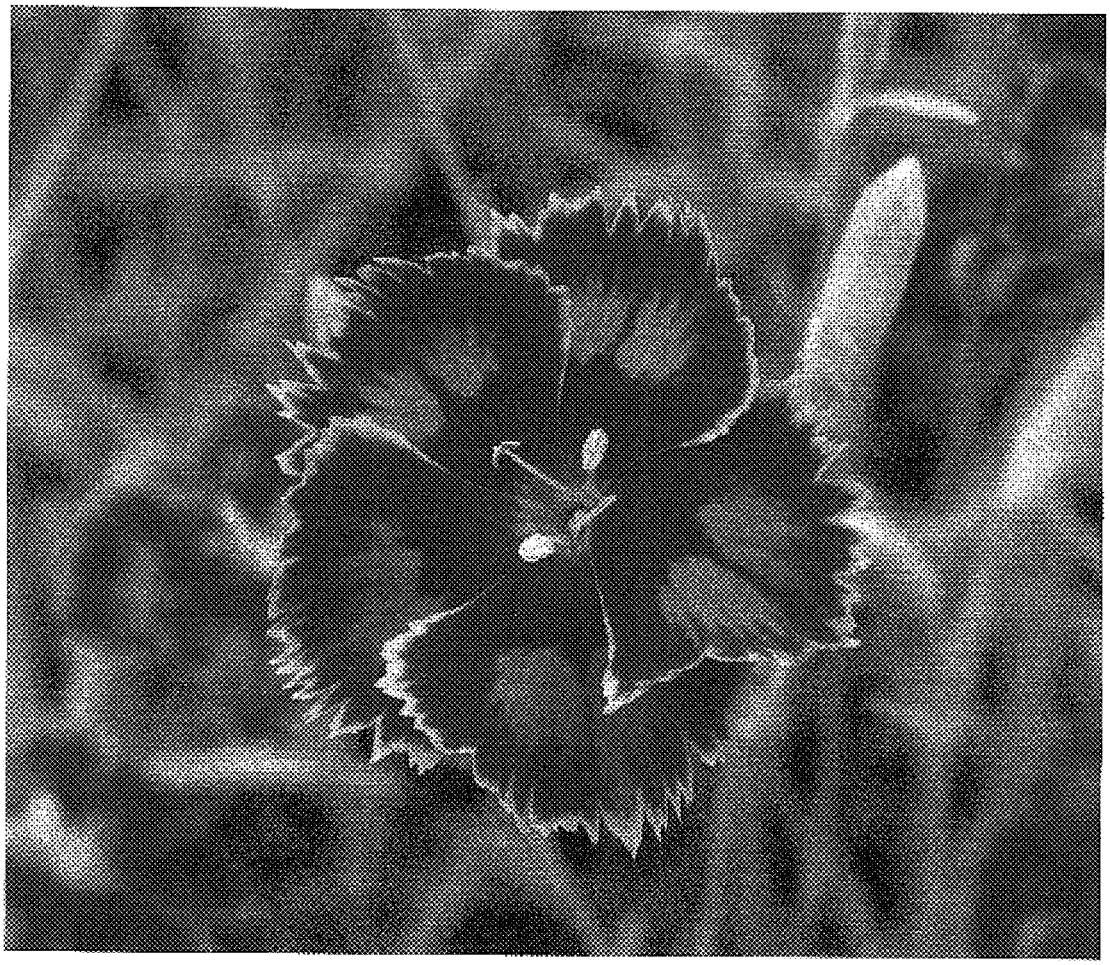

The drawing labeled as FIG. 2 is a close-up of flowers.

Figure 1:
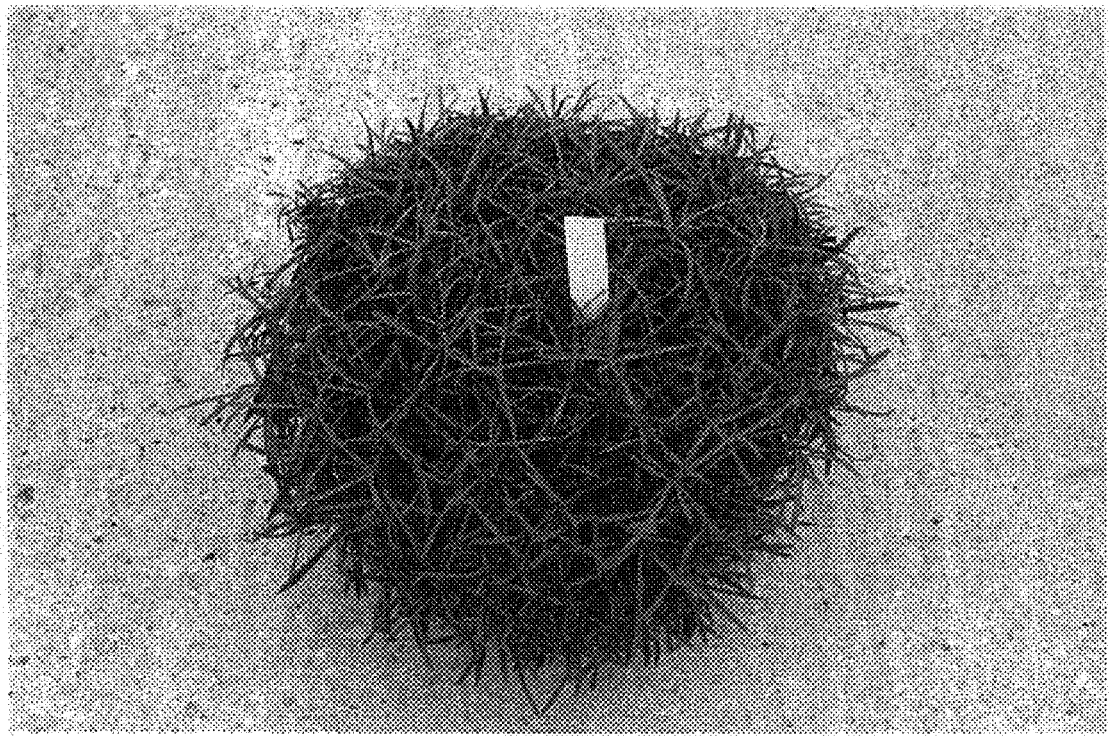

FIG. 1 was made of a plant grown in a 3 liter container and FIG. 2 was made of a plant grown in 1.5-liter container in a cold glasshouse in Devon, United Kingdom. No chemicals were used to treat the plant. The drawings were made using conventional techniques and although colors may appear different from actual colors due to light reflectance they are as accurate as possible by conventional photography. The age of the plant in FIG. 1 is 4–6 months of age, and in FIG. 2 is 9 months of age.

BOTANICAL DESCRIPTION OF THE PLANT

The following is a detailed description of the new cultivar 'STRAWBERRY SORBET'. Data was collected in spring from 1.5-liter container plants in spring, and grown indoors in Devon, United Kingdom. The color determinations are in accordance with the 2001 edition of The Royal Horticultural Society Colour Chart except where general color terms of ordinary dictionary significance are used. No chemicals were used to treat the plants. Growing conditions are typical to other *Dianthus*.

Botanical classification: *Dianthus* 'STRAWBERRY SORBET'.
Species: ×*hybrida*.
Common name: Dwarf carnation.
Commercial classification: *Dianthus* hybrid.
Type: Perennial herb.
Use: Used as a flowering plant for pots, containers and the garden.
Parentage: 'STRAWBERRY SORBET' is a complex hybrid plant that resulted from the open pollination between large families of seedlings from *Dianthus* 'Queen of Henri' (unpatented) and *Dianthus* 'Waithman's Beauty' (unpatented).
Plant description:
- *Bloom period.*—May through October.
- *Plant habit.*—Very compact.
- *Plant height.*—15 cm–20 cm in height at maturity.
- *Plant width.*—25 cm–35 cm in width at maturity.
- *Plant hardiness.*—Hardy to minus 15° Centrigrade.
- *Root system.*—Fine fibrous roots.
- *Propagation.*—Propagation is accomplished using vegetative cuttings.
- *Cultural requirements.*—Grow in full sun in well-drained, moderately fertile soil.
- *Diseases and pests.*—Susceptible to known *Dianthus* pests and disease but no other susceptibilities to pests or disease are known to the inventor.
- *Time and temperature needed to produce a rooted cutting.*—3 weeks are needed to produce roots on cuttings using a mist propagation unit with bottom heat of 21° Centigrade, and a minimum air temperature of 15° Centigrade.
- *Crop time.*—An average of 3 months in the spring and 6 months in the fall is needed to produce a finished container size plant from a well-rooted cutting.

Stem:
- *Shape.*—Cylindrical.
- *Stem dimensions.*—120 mm in length, and 3 mm in diameter.
- *Stem surface.*—Glabrous and glaucous.
- *Stem color.*—145B.
- *Branching.*—Numerous branching shoots from the axils of lower leaves.
- *Internode length.*—10 mm to 15 mm between nodes.
- *Node color.*—145C.
- *Node dimensions.*—4 mm in diameter and 3 mm in length.

Foliage:
- *Type.*—Evergreen.
- *Shape.*—Linear.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—80 mm in length and an average of 3 mm in width.
- *Leaf color* (*adaxial and abaxial surfaces*).—N133A.
- *Fragrance.*—Absent.

Flowers:
- *Inflorescence.*—Cymose.
- *Flower type.*—Salviform, double and symmetrical.
- *Flower dimensions* (*including calyx*).—30 mm in length and 40 in diameter.
- *Fragrance.*—Slightly clove-like.
- *Bud.*—Shape: Cylindrical. Dimensions: 20 mm in length, 6 mm in width. Color: 138C. Anthocyanin: Absent.
- *Petals.*—Persistent, single, apopetalous, slightly overlapping Number: Five petals. Margin: Crenate-dentate (toothed 2 mm deep). Shape: Obteltoid and slightly folded. Surface: Glabrous. Dimensions: 40 mm. in length and 20 mm. in width. Upper surface: Ground color of blade: 58B. Color of band around center: 59B. Color of middle of strap: 145B. Color of base of strap: 145D. Lower surface: Ground color of blade: 63B. Color of band around center: none. Color of middle of strap: 145B. Color of base of strap: 145D.
- *Calyx.*—Shape: cylindrical. Dimensions: 7 mm in diameter and 25 mm in length. Anthocyanin: Absent. Sepals: Five in number. Fused or unfused: Sepals fused. Color: 133A. Anthocyanin: Absent.
- *Peduncle dimensions.*—150 mm in length and 2 mm in diameter.
- *Peduncle color.*—N138C.
- *Peduncle surface.*—Glaucous.
- *Epicalyx.*—Present.
- *Bracts.*—Number: One pair (2 individual bracts). Dimensions: 6 mm in width and 10 mm in length. Color: 133A. Anthocyanin: Absent.
- *Bracteoles.*—Number: 1 pair (2 individual bracts). Dimensions: 5 mm in width, 10 mm in length. Color: 131A. Anthocyanin: Absent.
- *Lastingness of flower.*—Each individual flower lasts an average of 10 days on or off the plant at 20° centigrade.

Reproductive organs:

*Stamens.*—Number: 10. Dimensions: 30 mm in length and 1 mm in diameter. Color: 63D.

*Anther.*—Number: 10. Dimensions: 2 mm in length and 1 mm in diameter. Color: 63D. Attachment: Dorsi-fixed.

*Pollen.*—Present.

*Pollen color.*—190B.

*Pistil.*—One that divides into two above the ovary.

*Pistil dimensions.*—12 mm in length, 1 mm in width.

*Styles.*—Number: 2. Dimensions: 30 mm in length and 1 mm in width. Color: 190B.

*Stigma.*—Color: 73D. Height above petals: 15 mm above petals.

*Ovary.*—Position: Superior. Dimensions: 10 mm in length and 4 mm in diameter. Shape: Spindle shaped. Color: Upper 144B, lower 144D.

Seed:

*Seed.*—Present.

*Dimensions.*—2 mm in length, 1 mm in width.

*Shape.*—Flattened and wrinkled.

*Color.*—Black.

It is claimed:

1. A new and distinct cultivar of *Dianthus* plant named 'STRAWBERRY SORBET' as described and illustrated herein.

* * * * *